United States Patent [19]

Fujie et al.

[11] Patent Number: 5,547,934
[45] Date of Patent: * Aug. 20, 1996

[54] WF11243 SUBSTANCE

[75] Inventors: Akihiko Fujie, Tsuchiura; Shigehiro Takase, Ishioka; Michio Yamashita, Tsukuba; Tomoko Sato, Tsukuba; Seiji Hashimoto, Tsukuba; Masakuni Okuhara, Tsukuba, all of Japan

[73] Assignee: Fujisawa Pharmaceutical Co., Ltd., Osaka, Japan

[*] Notice: The term of this patent shall not extend beyond the expiration date of Pat. No. 5,446,022.

[21] Appl. No.: 429,636

[22] Filed: Apr. 27, 1995

Related U.S. Application Data

[63] Continuation of Ser. No. 140,074, filed as PCT/JP92/00586, May 8, 1992, Pat. No. 5,466,022.

[30] Foreign Application Priority Data

May 9, 1991 [JP] Japan ................... 3-132234
Oct. 21, 1991 [JP] Japan ................... 3-299552

[51] Int. Cl.$^6$ ............... C07K 11/02; C12P 21/02; C12M 1/14; A61K 38/12
[52] U.S. Cl. ............ 514/11; 424/118; 435/71.1; 435/254.1; 435/911; 514/9; 514/10; 530/317; 530/321; 530/323
[58] Field of Search ................. 514/11, 9, 10; 424/118; 435/71.1, 254.1, 911; 530/317, 323, 321

[56] References Cited

U.S. PATENT DOCUMENTS 5,446,022  8/1995  Fujie et al. ................. 514/11

FOREIGN PATENT DOCUMENTS 0405998  1/1991  European Pat. Off. .

*Primary Examiner*—Herbert J. Lilling
*Attorney, Agent, or Firm*—Oblon, Spivak, McClelland, Maier & Neustadt

[57] ABSTRACT

The present invention relates to a novel polypeptide having the following presumed structure:

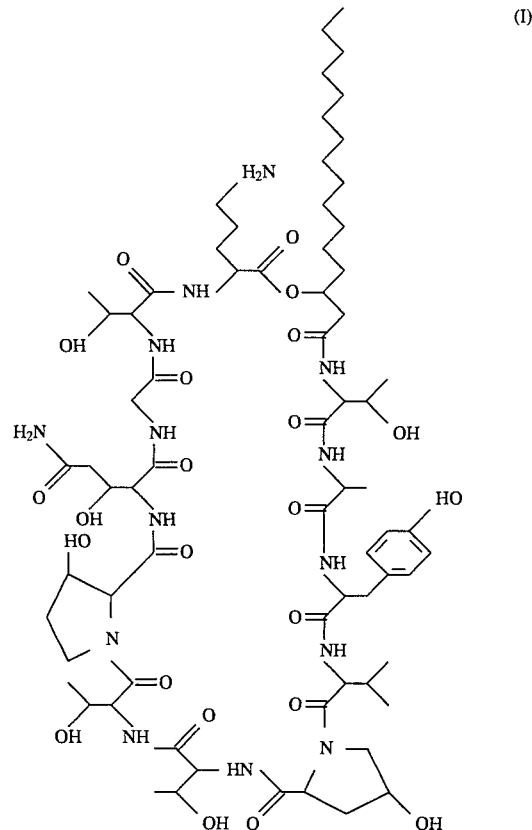

and the compound has both excellent fungicidal and protozoicidal effects.

7 Claims, 2 Drawing Sheets

WF11243 SUBSTANCE

This application is a continuation of application Ser. No. 08/140,074 filed Nov. 4, 1993, now U.S. Pat. No. 5,466,022, which is a 371 of PCT/JP92/00586 filed May 8, 1992.

FIELD OF THE INVENTION

The present invention relates to WF11243 substance and its salts as well as to a method of preparing them and use of them. The WF11243 substance is a novel substance which is isolated and purified from a culture broth of microorganisms, especially fungi. It has excellent fungicidal and protozoicidal activity and is, therefore, useful as various preventing and treating medicines for preventing, curing and reducing various diseases and disorders to be caused by fungi and protozoans. It is also useful for prevention and treatment of *Pneumocystis carinii* pneumonia.

Therefore, the present invention plays an important role in various technical fields of medicines, cosmetics, foods and drinks.

PRIOR ART

Hitherto, various fungicides have been obtained from cultures of microorganisms or by chemical syntheses. Some of them could be admitted to be good, but many of them have various problems, such as appearance of drug-tolerant microorganisms and safety of themselves. At present, no one has a satisfactory fungicidal agent which is completely free from the problems.

Recently, various diseases to be caused by protozoans, especially those to be caused by *Pneumocystis carinii* such as *Pneumocystis carinii* pneumonia, have been closed up, and development of methods of preventing and treating them has been strongly desired in this technical field.

PROBLEMS TO BE SOLVED BY THE INVENTION

The present invention has been made in view of the current technical situation as mentioned above, and the object of the present invention is to provide and develop a novel protozoicidal agent which is effective for preventing the growth of *Pneumocystis carinii* which causes *Pneumocystis carinii* pneumonia and other diseases, or protozoans. Another object of this invention is to develop and provide novel fungicides useful for preventing the growth of various fungi.

MEANS TO SOLVE THE PROBLEMS

In order to attain the above-mentioned object, the present inventors investigated from various aspects and noted natural substances, especially fermented products from microorganisms, in view of safety. They studied and investigated various microorganisms and, as a result, have found that fungal strain No. 11243 as isolated from fallen leaves samples collected in Ayabe-shi, Kyoto-fu, Japan, produces and accumulates the intended product in the culture broth. They have further studied in detail the product with respect to the physico-chemical properties thereof and have found that the product is a novel substance. They have named the substance WF11243 substance. Further, they have named the hydrochloride thereof FR901469 substance. After further study of the novel WF11243 substance, they have established an industrial method of producing them and have achieved the present invention.

Figure 1:
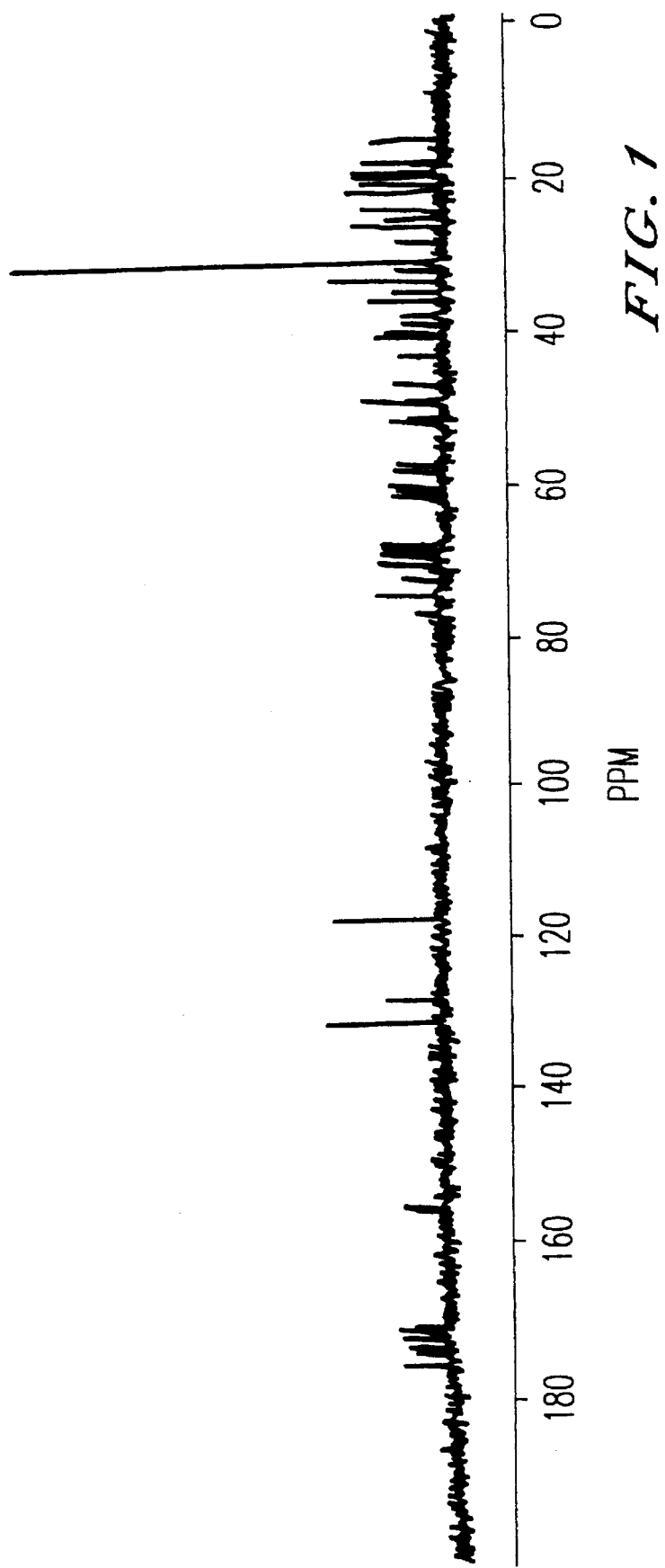
FIG. 1 shows a $^{13}C$ nuclear magnetic resonance spectrum of FR901469 substance.

The WF11243 substance of the present invention is a novel substance having, as its hydrochloride, FR901469 substance, the physico-chemical properties as mentioned below.

Physico-Chemical Properties of FR901469 Substance (1)

(1) Appearance:
  white power
(2) Melting point:
  182° to 187° C.
(3) Specific rotation:
  $[\alpha]_D^{23}$ +29° (c=1.5, methanol)
(4) Molecular formula:
  $C_{71}H_{116}N_{14}O_{23} \cdot HCl$
(5) Element analysis:
  Calcd (%): for $C_{71}H_{116}N_{14}O_{23} \cdot HCl \cdot 8 H_2O$ C 49.74, H 7.82, N 11.44
  Found (%): C 49.65, H 7.72, N 11.40
(6) Solubility:
  soluble: methanol, water
  slightly soluble: acetone
  insoluble: n-hexane
(7) Color reaction:
  positive: iodine vapor reaction, ceric sulfate reaction, ninhydrin reaction
  negative: Molish reaction, Ehrlich reaction
(8) Thin layer chromatography (TLC):

| Stationary phase | Developing solvent | Rf value |
|---|---|---|
| Silica gel 60 $F_{254}$ (made by E. Merck) | n-butanol/acetic acid/water (4/1/2) | 0.42 |
| RP-18 $WF_{254}S$ (made by E. Merck) | 45% aqueous acetonitrile (containing 0.5% $NH_4H_2PO_4$) | 0.18 |

(9) Infrared absorption spectrum (FT-IR (KBr)):
  Significant peaks are: $\nu_{max}^{KBr}$: 3400, 2920, 1730, 1660, 1650, 1635, 1540, 1520, 1460, 1250, 1090 cm$^1$
(10) High performance liquid chromatography (HPLC):
  column: YMC.Pack ODS-AM (AM-303, S-5, 120A, 4.6 mm ID×250 mm; YMC Co., Ltd. )
  detection: 210 nm
  developing solvent: 45% aqueous acetonitrile (containing 0.5% $NH_4H_2PO_4$)
  flow rate: 1 ml/min
  retention time (RT): 10.9 min
(11) $^{13}C$ Nuclear magnetic resonance spectrum (100 MHz, $CD_3OD$):
  FIG. 1 shows the chart.
  δc: 176.1 (s), 174.6 (s), 174.0 (s), 173.8 (s), 173.4 (s), 172.8 (s), 172.6 (s), 172.5 (s), 172.4 (s), 172.1 (s), 171.9 (s), 171.8 (s), 171.7 (s), 171.2 (s), 156.1 (s), 131.4 (d) ×2, 128.6 (s), 117.9 (d) ×2, 74.2 (d), 72.0 (d), 70.5 (d), 70.1 (d), 70.0 (d), 69.1 (d), 68.8 (d), 68.3 (d), 67.7 (d), 61.4 (d), 60.9 (d), 60.3 (d), 59.8 (d), 58.2 (d), 57.9 (t), 57.6 (d), 57.2 (d), 56.8 (d), 51.7

(d), 50.8 (d), 46.4 (t), 43.1 (t), 42.9 (t), 40.4 (t), 39.9 (t), 38.9 (t), 37.6 (t), 35.8 (t), 34.7 (t), 33.1 (t), 31.6 (d), 30.8 (t), 30.7 (t), 30.7 (t), 30.7 (t), 30.6 (t), 30.5 (t), 30.4 (t), 30.3 (t), 28.1 (t), 25.9 (t), 24.9 (t), 23.7 (t), 21.2 (q), 20.9 (q), 20.3 (q), 19.2 (q), 18.9 (q), 18.7 (q), 17.2 (q), 14.4 (q).

Figure 2:
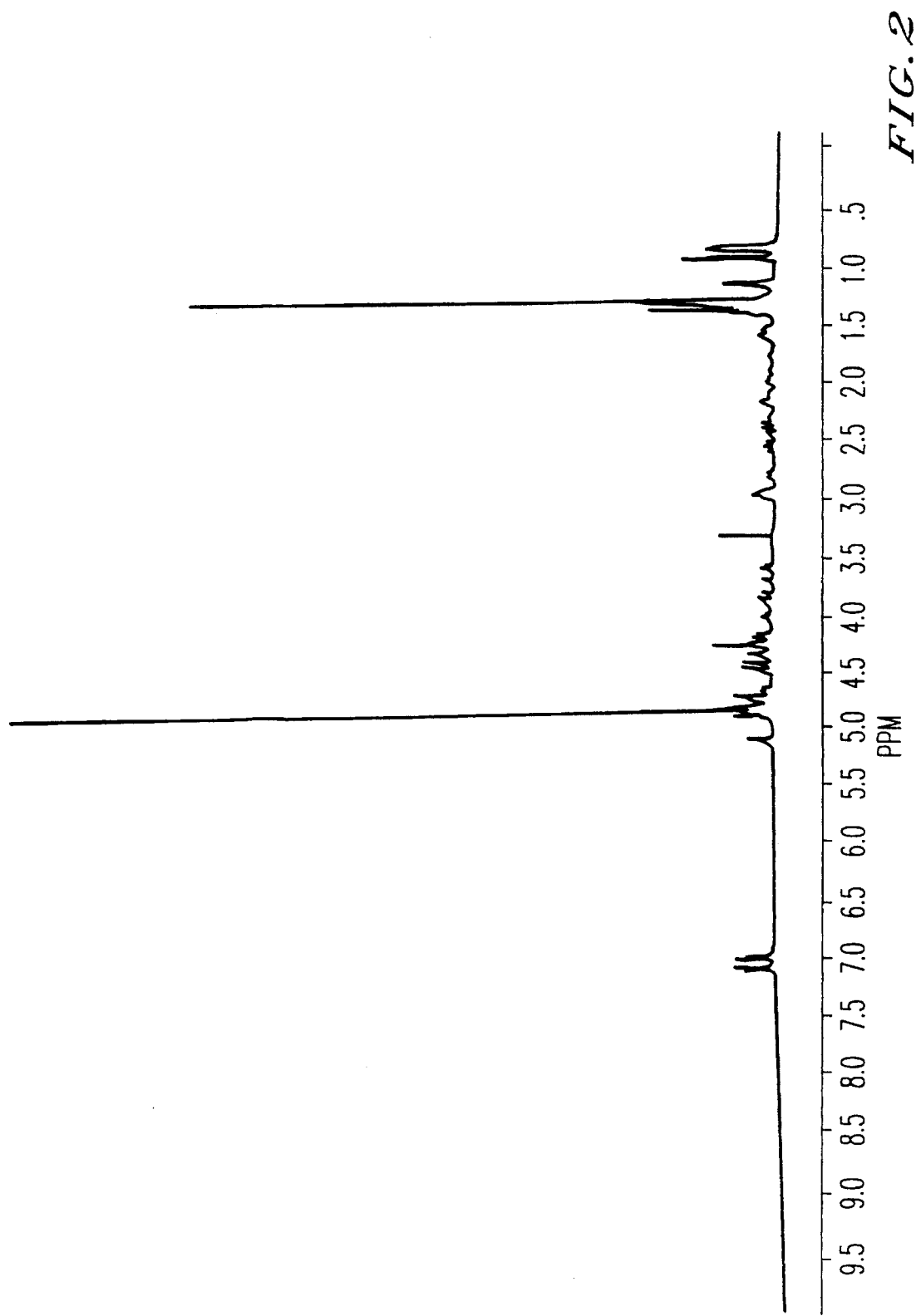
FIG. 2 is $^{1}H$ nuclear magnetic resonance spectrum of FR901469 substance.

(12) $^1$H Nuclear magnetic resonance spectrum (400 MHz, $CD_3OD$):

FIG. 2 shows the chart.

δH: 7.08 (2H, d, J=8 Hz), 6.98 (2H, d, J=8 Hz), 5.18–5.09 (2H, m), 4.88 (1H, br s), 4.76–4.69 (3H, m), 4.65 (1H, m), 4.48 (1H, m), 4.46 (1H, d, J=5 Hz), 4.41 (1H, d, J=9 Hz), 4.36–4.27 (3H, m), 4.24–4.13 (6H, m), 3.98 (1H, m), 3.92–3.78 (3H, m), 3.70 (1H, dd, J=11 and 4 Hz), 3.58 (1H, br d, J=11 Hz), 3.00–2.93 (3H, m), 2.80 (1H, dd, J=13 and 11 Hz), 2.56 (1H, dd, J=13 and 11 Hz), 2.45 (1H, dd, J=14 and 9 Hz), 2.37 (1H, br d, J=13 Hz), 2.30 (1H, m), 2.21–2.05 (3H, m), 2.03–1.93 (2H, m), 1.89 (1H, m), 1.77 (1H, m), 1.62–1.50 (4H, m), 1.39 (3H, d, J=6 Hz), 1.35 (3H, d, J=6.5 Hz), 1.35 (3H, d, J=6.5 Hz), 1.30 (3H, d, J=6 Hz), 1.28 (22H, m), 1.13 (3H, d, J=6 Hz), 0.89 (3H, t, J=7 Hz), 0.81 (3H, d, J=6.5 Hz), 0.80 (3H, d, J=6.5 Hz),

(13) Molecular formula and FAB-MS:

$C_{71}H_{116}N_{14}O_{23}$·HCl FAB-MS m/z 1533 (M+H)$^+$; HRFAB-MS m/z 1555.8240 (calcd for $C_{71}H_{116}N_{14}O_{23}$Na: 1555.8235)

(14) Analysis of amino acids:

Thr (4), Gly (1), Ala (1), Val (1), Tyr (1), Orn (1) (as hydrolyzed in 6N HCl at 110° C. for 20 hours)

(15) Ultraviolet absorption spectrum:

Significant peaks are: $\lambda_{max}^{H_2O}$: 225 (sh), 275 (1200), 280 (sh) nm $\lambda_{max}^{0.01N\ HCl}$: 225 (sh), 275, 280 (sh) nm $\lambda_{max}^{0.01N\ NaOH}$: 240, 292 nm From the above-mentioned physico-chemical properties, the WF11243 substance of the present invention was recognized to have polypeptide-like characteristics. As a result of an attempt to determine the structure of the substance, the present inventors have succeeded in the elucidation to obtain the following presumed structural formula (I) for the substance:

from fallen leaves collected by the present inventors in Ayabe-shi, Kyoto-fu, and may be also produced by chemical syntheses such as peptide synthesis. This organism grew restrictedly on various culture media, and formed pale orange colonies. Its mycological characteristics were as follows.

Cultural characteristics on various agar media are summarized in Table 1. After innoculating at the center on a malt extract agar medium, the culture grew very restrictedly attaining 0.5 to 1.0 cm in diameter after two weeks at 25° C. This colony surface was raised and pale orange and it produced hyaline mucous exudation. The reverse was grayish orange. Conidial structures were observed. Colonies on potato dextrose agar grew very restrictedly, attaining 0.5 to 1.0 cm in diameter, under the same condition. The surface was raised, radially sulcate and pale orange and it produced hyaline mucous exudation. The reverse was pale yellow. Anamorphosis (conidial structures) formed.

TABLE 1

| Cultural characteristics of the Strain No. 11243 | |
|---|---|
| Medium | Cultural characteristics |
| Malt extract agar | G: Very restrictedly, 0.5 to 1.0 cm in diameter |
| | S: Circular, raised, formed conidial structures, produced hyaline mucous exudation, pale orange (5A3) |
| | R: Grayish orange (5B4) |
| Potato dextrose agar | G: Very restrictedly, 0.5 to 1.0 cm in diameter |
| | S: Circular, raised, radially sulcate, formed conidial structures, produced hyaline mucous exudation, pale orange (5A3) |
| | R: Pale Yellow (4A3) |
| Czapek-Doc agar | G: Very restrictedly, 0.1 to 0.5 cm in diameter |
| | S: Circular, plane, thin, formed conidial structures, orange white (5A2) |
| | R: Yellowish gray (4B2) |

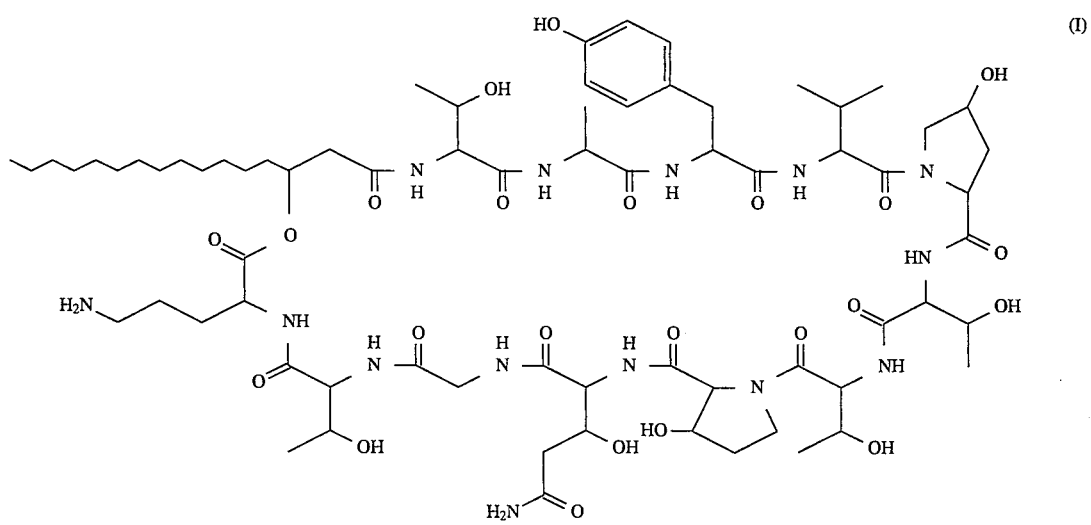

(I)

The WF11243 substance of the present invention is produced, for example, by the fungus strain No. 11243 isolated TABLE 1-continued Cultural characteristics of the Strain No. 11243

| Medium | Cultural characteristics |
|---|---|
| Sabouraud agar | G: Very restrictedly, 0.5 to 1.0 cm in diameter<br>S: Circular, raised, radially sulcate, formed no conidial structures, produced hyaline mucous exudation, grayish orange (5B3)<br>R: Brown (6E7) |
| Oatmeal agar | G: Very restrictedly, 0.5 to 1.0 cm in diameter<br>S: Circular to irregular, radially sulcate, formed conidial structures, orange white (5A2) black at center<br>R: Pale Yellow (4A3) |
| Yp Ss agar | G: Very restrictedly, 0.5 to 1.0 cm in diameter<br>S: Circular, raised, radially sulcate, formed no conidial structures, produced hyaline mucous exudation, light orange (5A4)<br>R: Pale Yellow (4A3) |
| Corn meal agar | G: Very restrictedly, 0.5 to 1.0 cm in diameter<br>S: Circular to irregular, radially sulcate, formed conidial structures, produced hyaline mucous exudation, orange white (5A2), dark brown (6F8) at center<br>R: Dark Gray (1F1) |
| MY20 agar | G: Very restrictedly, 0.1 to 0.5 cm in diameter<br>S: Irregular, raised, wrinkly, formed conidial structures, produced hyaline mucous exudation, light orange (5A4)<br>R: Light orange (5A4) |

Abbreviation
G: growth
S: colony surface
R: reverse

These characteristics were observed after 14 days of incubation at 25° C. The color description were based on the Methuen Handbook of Colour(1). (1) Kornerup, A. and J. H. Wanscher: Methuen Handbook of Colour (3rd ed.), Methuen, London, 1983.

The No. 11243 strain may grow at 7° to 29° C., and the optimum growth temperature for the strain is 22° to 26° C. (as measured on a potato dextrose agar).

Totally considering these characteristics, we identified that the No. 11243 strain belongs to the group of fungi and named it No. 11243. This was deposited with National Institute of Bioscience and Human-Technology-p-Agency of Industrial Science and Technology, Ministry of International Trade and Industry (Deposit No.: FERM BP-3373; Deposit date: Apr. 23, 1991).

It should be understood that production of the WF11243 substance is not restricted to only the use of the particular microorganism which has been referred to herein only for explanation of producing the substance. The present invention includes use of all artificial and natural variants and mutants capable of producing the WF11243 substance, which may be obtained by variation or mutation of the microorganism of the described strain by X-ray irradiation or ultraviolet irradiation or by treatment with N-methyl-N'-nitro-N-nitrosoguanidine, 2-aminopurine or the like.

The WF11243 substance of the present invention can be produced by inoculating fungi of producing the substance (for example, strain No. 11243) in a nutrient medium containing assimilatable carbon and nitrogen sources and incubating them therein under an aerobic condition (for example, by shaking culture or submerged aerobic culture).

As usable carbon sources, preferred are glucose, sucrose, starch, modified starch, fructose, glycerin and other hydrocarbons.

As usable nitrogen sources, preferred are oatmeal, yeast extract, peptone, gluten meal, cotton seed flour, cotton seed refuse, soybean meal, corn steep liquor, dried yeast, wheat germ, peanut meal, chicken bone meal, etc. In addition, also advantageously usable are inorganic and organic nitrogen compounds, such as ammonium salts (for example, ammonium nitrate, ammonium sulfate, ammonium phosphate, etc.), ureas and amino acids.

These carbon sources and nitrogen sources are advantageously employed in combination, but they are not always needed to be pure. This is because some impure sources of these kinds would often contain growth factors or micro nutrients, advantageously.

If desired, inorganic salts, for example, those mentioned below could be added to the medium. Such salts include sodium carbonate, potassium carbonate, sodium phosphate, potassium phosphate, sodium chloride, potassium chloride, sodium iodide, potassium iodide, magnesium salts, copper salts, cobalt salts, etc.

If the medium used foams noticeably, liquid paraffin, animal oil, vegetable oil, mineral oil, silicone or the like may be added thereto, as the case may be.

Where industrial mass-production of a large amount of the intended product is desired, submerged aerobic culture of the microorganisms is recommended, like the case of producing other fermented products. Where production of a small amount of it is desired, shaking culture using a flask is preferred.

Where the culture of the microorganisms of producing the intended WF11243 substance is effected in a large tank, it is desired that the microorganisms are first inoculated and incubated in a relatively small amount of a medium and then the resulting culture is transferred to a large-sized production tank to further incubate it therein, for the purpose of preventing retardation of the growth of the cultivated microorganisms in the step of producing the intended WF11243 substance. In the case, the composition of the medium to be used for the pre-culture may be same as or different from, if desired, that of the medium to be used for the production culture.

Culture of the microorganisms is preferably effected under an aerobic stirring condition, to which any and every known means may be applied. For instance, employable is stirring with propellers or other machines, or rotation or shaking of fermenters, or pumping, or air blowing. The air to be used for aeration is a sterilized one.

The incubation temperature may suitably be varied within the range at which the WF11243 substance-producing microorganisms of the present invention may produce the intended substance of the invention. In general, it is from 1° to 40° C., preferably from 14° to 36° C. The culture time varies, depending upon the culture condition and the amount of the microorganisms to be inoculated. In general, it is approximately from one day to one week.

After fermentation, the intended WF11243 substance is collected from the culture broth. Briefly, the cultured fungi are directly extracted with water and/or organic solvent or, after broken by mechanical, ultrasonic or the like known means, extracted with water and/or organic solvents. Then, WF11243 substance is isolated and purified by ordinary methods. In the case of the culture broth, WF11243 substance is recovered directly and then purified by ordinary methods.

As isolating and purifying methods, for example, suitable are a solvent extraction method with water, organic solvent or mixed solvents of them, a chromatographic method, and a recrystallization method from single solvents or mixed solvents. Such ordinary methods may be combined.

Isolation and purification of the WF11243 substance produced may suitably be effected by means of the above-mentioned known methods. The substance may be isolated and purified, for example, by the following method. Briefly, the culture is extracted with an aqueous acetone, adsorbed to a neutral adsorbing resin (for examples, HP-20, made by Mitsubishi Kasei Corp., Japan) under a neutral condition, eluted with an acidified aqueous acetone, concentrated, washed with ethyl acetate, and extracted with butanol. If desired, the adsorption-desorption with the neutral adsorbing resin may be repeated. Thus, the intended product is collected as a pure form. The WF11243 substance is an amphoteric substance and therefore may react with a base or an acid to form a salt. The WF11243 substance may be recovered and purified even as its free form (WF11243 substance of itself) or may also be recovered and purified as its salt. They (free form, salt) may be converted to each other by any known methods.

AS salts of the WF11243 substance with bases, there are mentioned alkali metal salts such as sodium salt or potassium salts, and alkaline earth metal salts such as calcium salt or magnesium salt, and salts with inorganic bases such as ammonium salt, and salts with organic bases, such as organic amine salts including methylamine salt, ethylamine salt, propylamine salt, iso-propylamine salt, butylamine salt, t-butylamine salt, dimethylamine salt, diethylamine salt, trimethylamine salt, triethylamine salt, pyridine salt, picoline salt, dicyclohexylamine salt, N,N'-dibenzylethylenediamine salt and amino acid salts including arginine salt, asparagine salt and glutamic acid salt. As salts thereof with acids, there are exemplified inorganic acid-addition salts such as hydrochloric acid salt, hydrobromic acid salt, hydroiodic acid salt, sulfuric acid salt, nitric acid salt and phosphoric acid salt, organic acid-addition salts such as acetic acid salt, trifluoroacetic acid salt, maleic acid salt, tartaric acid salt, methanesulfonic acid salt, benzenesulfonic acid salt, formic acid salt and toluenesulfonic acid salt, and amino acid-addition salts such as aspattic acid salt and glutamic acid salt, etc.

The present invention also provides a pharmaceutical composition containing the WF11243 substance and/or its salt as an active ingredient. It can be used in the form of a pharmaceutical preparation, for example, in solid, semisolid or liquid form, which contains the WF11243 substance and/or its salt, as an active ingredient, in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation.

The active ingredient may be compounded, for example, with ordinary non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and flavours may be used.

The WF11243 substance and/or its salt are/is included in the pharmaceutical composition in an amount sufficient to produce the desired effect to the process or status of diseases.

For applying the composition to human beings, it is preferable to apply it by intravenous, intramuscular, or oral administration. While the dosage of the therapeutically effective amount of the active ingredient varies and depends upon the age and condition of each individual patient to be treated; in the case of intravenous administration, a daily dose of from 0.01 to 100 mg of the active ingredient per kg weight of a human being, in the case of intramuscular administration, a daily dose of from 0.1 to 100 mg of the active ingredient per kg weight of a human being, in case of oral administration, a daily dose of from 0.5 to 100 mg of the active ingredient per kg weight of a human being is generally given for prevention or treatment of infectious diseases in human beings.

The WF11243 substance and/or its salts of the present invention are/is widely effective for prevention and/or treatment of various fungal infectious diseases and they are also effective for prevention and/or treatment of other various protozoiases to be caused by various protozoans. In particular, they are effective for prevention and/or treatment of various *Pneumocystis carinii* infections (e.g., *Pneumocystis carinii* pneumonia). In use of the WF11243 substance and/or its salts of the present invention for prevention and/or treatment of *Pneumocystis carinii* pneumonia, the following points are to be noted.

For administration by inhalation, the compounds of the present invention are conveniently delivered in the form of an aerosol spray presentation from pressurized packs or nebulisers. The compounds may also be delivered as powders which may be formulated and the powder compositions may be inhaled with the aid of an insufflation powder inhaler device. The preferred delivery system for inhalation is a metered dose inhalation aerosol, which may be formulated as a suspension or solution of the compound in suitable propellants such as fluorocarbons or hydrocarbons.

Because of desirability to directly treat lung and bronchi, aerosol administration is a preferred method of administration. Insufflation is also a desirable method, especially where infection may have spread to ears and other body cavities.

Alternatively, parenteral administration may be employed using drip intravenous administration.

The present invention will be explained in more detail by way of the following examples.

EXAMPLE 1

1) Fermenting Production of WFl1243 Substance 160 ml of a pre-culture medium comprising 4% of sucrose, 2% of cotton seed oil refuse, 1% of dried yeast, 1% of peptone, 0.2% of $KH_2PO_4$, 0.2% of $CaCO_3$ and 0.1% of Tween 80 was put into each 500 ml-Erlenmeyer flask and sterilized at 121° C. for 30 minutes. One loop of a slant-culture of fungal strain No. 11243 (FERM BP-3373) was inoculated to each medium and incubated at 25° C. for 4 days by shaking cultivation.

Next, a fermenting medium comprising 2% of modified starch, 0.5% of glucose, 1% of cotton seed oil refuse, 1% of gluten meal, 2% of $KH_2PO_4$, 1.5% of $Na_2HPO_4.12H_2O$, 0.001% of $ZnSO_4.7H_2O$, 0.025% of Adekanol LG-109 (made by Asahi Denka Co., Japan) and 0.025% of Silicone KM70 (made by Shin-etsu Chemical Co., Japan) was prepared, and 20 liters of the medium was put in a 30-liter jar fermenter. This was sterilized at 121° C. for 30 minutes, and 2% of the previously obtained pre-culture was inoculated thereto and incubated at 25° C. for 4 days. Stirring of the medium was effected at 200 rpm and the amount of air introduced into the fermenter was 20 liter/min, during culture. The amount of the WF11243 substance as produced in the culture was determined by HPLC (column: Hibar LiChrosper 100 RP 18, made by E. Merck; solvent: 50% aqueous acetonitrile containing 0.5% of $NH_4H_2PO_4$; detection: UV 210 nm; flow rate: 1 ml/min). The same amount of acetone was added to the liquid culture, the resulting mix was filtered, and the filtrate was concentrated to a determined concentration. The resulting concentrate was used as a sample for determination.

(2) Extraction and Purification of WF11243 Substance

The same amount of acetone was added to 75 liters of the culture broth as obtained by the above-mentioned cultivation method and left at room temperature overnight with intermittently stirring the mix. This was filtered to obtain a culture extract. 65 liters of water was added to the liquid extract, followed by adjustment to have pH 6.5 with 6N NaOH. This was then applied to 6.5 liters of HP-20 column (made by Mitsubishi Kasei Corp., Japan). After the column was washed with 35 liters of water and 27 liters of 40% aqueous acetone, and the intended product was eluted with 48 liters of 80% aqueous acetone containing, as a final concentration, 0.002N HCl.

Purification was effected with on the basis of the fungicidal activity to *Candida albicans* as well as by HPLC (column: YMC Packed Column AM-303 (S-5, 120 A, ODS), made by YMC Co., Ltd.; mobile phase: 45% aqueous acetonitrile containing 0.5% $NH_4H_2PO_4$; detection: UV 210 nm; flow rate: 1 ml/min; retention time (RT): 10.9 min).

The eluate as obtained in the above was concentrated to 1.9 liters under reduced pressure, and it was adjusted to have pH of 6.0 and then washed with a double amount of ethyl acetate. Next, the active component was extracted out with 1.9 liters of butanol, and this was concentrated under reduced pressure and substituted by one liter of water. The resulting aqueous solution was adjusted to have pH 3.0 with 1N HCl and again washed with one liter of ethyl acetate, then it was extracted with one liter of butanol to isolate the active component therefrom. The organic solvent layer was washed with one liter of 1% sodium bicarbonate and one liter of aqueous hydrochloric acid having pH 4, then the organic solvent layer was concentrated under reduced pressure. Next, the residue was dissolved in 3.0 liters of 50% aqueous acetonitrile and applied to a 1.3 liter HP-20 column. The column was washed with 3.5 liters of water, 3.5 liters of 50% aqueous methanol, 3.5 liters of 80% aqueous methanol and 3.8 liters of methanol, and the active component was eluted out therefrom with 2.7 liters of 80% aqueous acetone containing, as a final concentration, 0.002N HCl. Next, the resulting eluate was concentrated under reduced pressure, the residue was dissolved in 5 liters of 20% aqueous methanol, and the solution was applied to a 500 ml-column of a reversed phase carrier (YMC Gel, ODS-AM, 120-S50, made by YMC Co., Ltd.). The column had previously been equilibrated with 20% aqueous acetonitrile containing 0.5% $NH_4H_2PO_4$. After the solution containing the intended product was charged in the column, the column was washed with one liter of 30% aqueous acetonitrile containing 0.5% $NH_4H_2PO_4$, one liter of 35% aqueous acetonitrile containing 0.5% $NH_4H_2PO_4$, and one liter of 40% aqueous acetonitrile containing 0.5% $NH_4H_2PO_4$. The intended product was eluted out with two liters of 45% aqueous acetonitrile containing 0.5% $NH_4H_2PO_4$.

280 ml of the thus eluted active fraction was diluted with the same amount of water and again applied to a 180 ml-column of a reversed phase carrier (YMC Gel, ODS-AM, 120-S50). After the column was washed with 0.4 liter of 30% aqueous acetonitrile containing 0.5% $NH_4H_2PO_4$, 0.4 liter of 35% aqueous acetonitrile containing 0.5% $NH_4H_2PO_4$ and 0.4 liter of 40% aqueous acetonitrile containing 0.5% $NH_4H_2PO_4$, it was developed with 43% aqueous acetonitrile containing 0.5% $NH_4H_2PO_4$ to elude the intended substance. 55 ml of the eluted active fraction was diluted with the same amount of water and then applied to a 40 ml-column of HP-20. The column was washed with 180 ml of water and the intended product was eluted with 100 ml of 80% aqueous acetone containing, as a final concentration, 0.002N HCl. The resulting eluate was concentrated under reduced pressure and, after acetone was removed, freeze-dried to obtain 72 mg of a white powder of hydrochloride of WF11243 substance. This is called FR901469 substance.

(3) Physico-chemical Properties of FR901469 Substance

Physico-chemical properties of FR901469 substance thus obtained are shown. Analysis of amino acids was effected in the manner as mentioned below. One mg of FR901469 substance was hydrolyzed with one ml of 6N HCl in a sealed tube at 110° C. for 20 hours. After hydrolysis, the reaction mixture was evaporated to dryness, and the resulting solid was analyzed with an amino acid analyzer (Hitachi 835 Automatic Amino-Acid Analyzer). The result indicated that the product comprised Thr (4), Gly (1), Ala (1), Val (1), Tyr (1), and Orn (1). The chemical structure of the product was determined to be as follows:

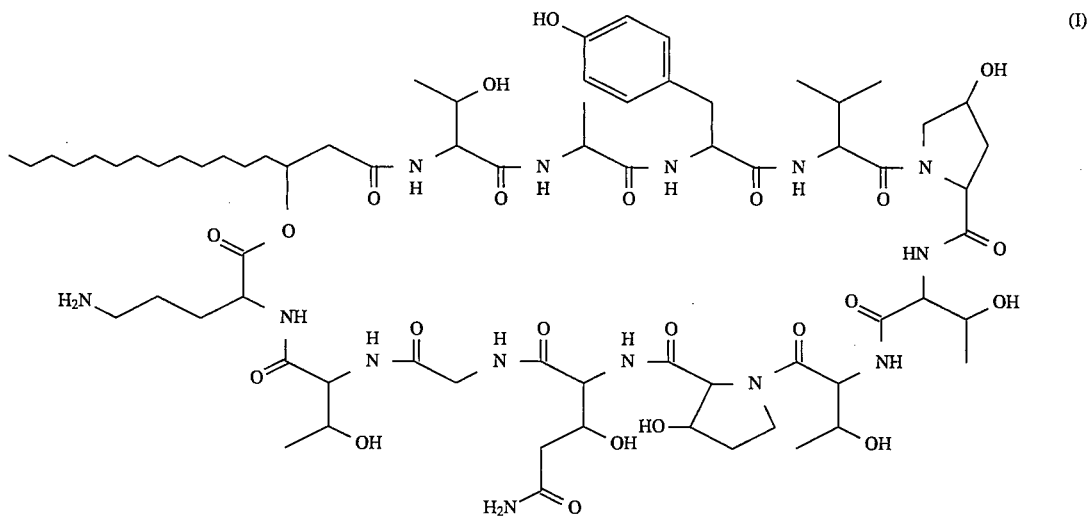

EXAMPLE 2

Biological Properties of FR901469 Substance (1) Microbicidal Activity:

The microbicidal activity of the FR901469 substance was measured by an ordinary microbroth dilution method using a 96-well multi-tray, which is mentioned below.

Microorganisms to be tested (mentioned below) were incubated on a slant medium. From the thus incubated cells, a test cell suspension (containing $2\times10^5$ living cells per ml) was prepared with an yeast nitrogen base dextrose (YNBD) medium. A continuous ½ diluted series of the FR901469 substance in YNBD was prepared and 100 µl was put in each well, and further 100 µl of the test cell suspension was added thereto and incubated therein at 37° C. for 24 hours (for Candida and Asperqillus), or for 48 hours (for Cryptococcus). After incubation, the turbidity of each well was measured, and the concentration of the active substance indicating a half (½) of the turbidity of the control well (not containing the active substance) was represented as the 50% growth inhibiting concentration ($IC_{50}$). The results obtained are shown in Table 2 below.

TABLE 2

Microbicidal Activity of FR901469 Substance

| Tested Microorganisms | $IC_{50}$ (µg/ml) |
|---|---|
| *Candida albicans* | |
| FP582 | <0.0093 |
| FP578 | 0.16 |
| FP629 | 0.16 |
| FP633 | 0.16 |
| Candida utilis YC123 | 0.16 |
| Candida krusei YC109 | 0.0039 |
| Candida tropicalis YC118 | 0.0039 |
| Cryptococcus neoformans YC203 | >10 |
| Aspergillus fumigatus 8004 | <0.0093 |
| Aspergillus niger ATCC9642 | 0.63 |

(2) Preventing effect of FR901469 Substance on a mouse *Candida albicans* infection:

The in vivo effectiveness of FR901469 substance as a fungicide was demonstrated by the experiment mentioned below.

4-week ICR female mice (body weight: 18 to 21 g) were used as test animals. One test group comprised five mice. A suspension of living cells of *Candida albicans* FP633 as suspended in a physiological saline solution was injected to the vein of the tail of each mice in an amount of $2\times10^6$ living cells per mouse, whereby all mice were infected with the fungi. One hour after infection, an aqueous physiological saline solution of FR901469 substance was subcutaneously injected to each mouse. The subcutaneous injection was repeated once a day for continuous 3 days from the next day of infection. On Day 14 after infection, the number of the living mice was counted. The results obtained are shown in Table 3 below.

TABLE 3

In vivo preventing effect of FR901469 substance on infection

| Dose (mg/kg) of FR901469 Substance | Number of Living Mice |
|---|---|
| 10 | 5 |
| 1 | 5 |
| 0 | 0 |

(3) Toxicity Test:

100 mg/kg of FR901469 substance was intraperitoneally injected to each of five 5-week ICR female mice, once a day, for continuous 3 days. As a result, no mice died. The body weight increase of all the test mice was same as that of the mice of a control group to which the substance was not injected. Thus, the high safety of the WF11243 substance was verified.

EXAMPLE 3

Preparation of Injection

| | |
|---|---|
| (1) FR901469 substance prepared in Example 1 | 5 g |
| (2) Edible salt (NaCl) | 9 g |
| (3) Sodium hydrogencarbonate | 1 g |

All the components (1) to (3) were dissolved in 100 ml of distilled water and 1 ml was put into each ampule to prepare 1000 ampules for injection.

EXAMPLE 4

Preparation of Aerosol for Inhalation

2% by weight of the compound of formula (I), 33% by weight of ethanol, and 65% by weight of a propellant (mixture of propane/isobutane=70/30) were charged into a valve-equipped pressure container to prepare an aerosol for inhalation.

EFFECT OF THE INVENTION

The present invention provides WF11243 substance, which is an unknown novel physiologically active substance. It displays excellent fungicidal and protozoicidal activity and is extremely useful for inhibition of the growth of fungi and protozoans and also for killing them in various technical fields of medicines, cosmetics, industrial drugs and, foods and drinks. The substance of the present invention is characterized in that it has both fungicidal activity and protozoicidal activity. Regarding the latter activity, for example, the substance is also characterized by the outstanding effectiveness for prevention and treatment of *Pneumocystis carinii* pneumonia.

In addition, since the structure of the active ingredient of the present invention has been presumed, industrial production of the substance by organic synthesis may be possible, as well as industrial production using microorganisms. As a result, production of various derivatives of the substance may be possible. Under the situation, production of many novel compounds and development of new uses of them can expected much.

References to the microorganism deposited under Rule 13.2
1. No. 11243
    (a) Name and Address of the depository with which said microorganism is deposited.
        Name: National Institute of Bioscience and Human-Technology of Industrial Science and Technology, Ministry of International Trade and Industry
        Address: 1–3, Higashi 1 chome, Tsukuba-shi, Ibaraki-ken, 305, Japan
    (b) Date on which the deposition was made: Apr. 23, 1991
    (c) Deposit No. (Accession No.) assigned to the deposit by the depository (a): FERM BP-3373.

We claim:
1. An isolated compound having formula (I):

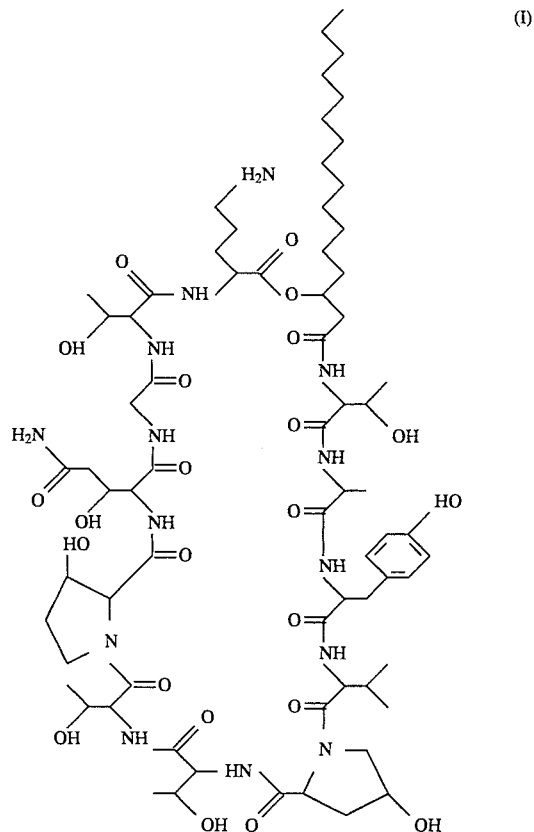

or a salt thereof.

2. A method for producing a compound of formula (I):

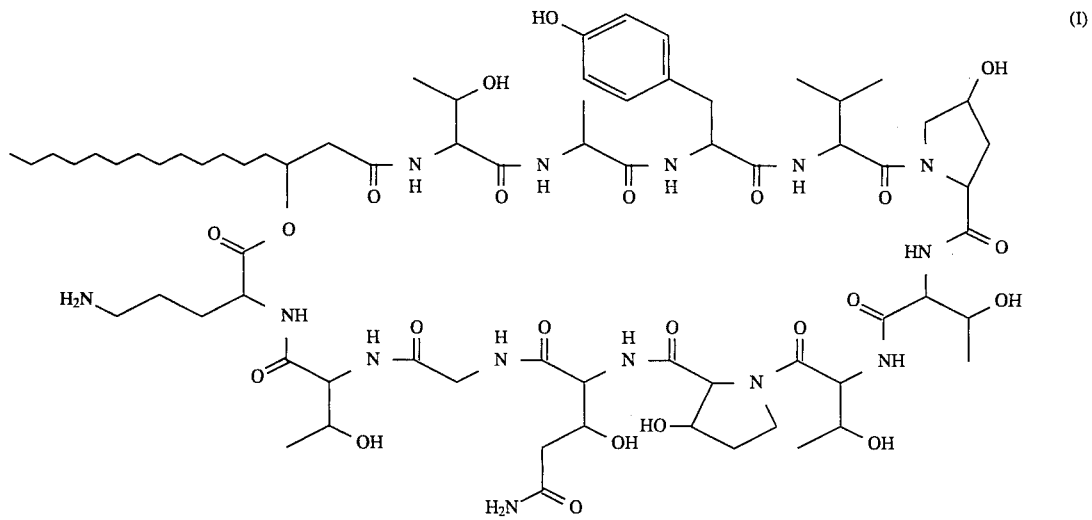

or a salt thereof which comprises: culturing FERM BP-3373 in a medium and collecting the compound of formula (I) or a salt thereof.

3. A purified cell culture containing a microorganism which produces a compound of formula (I):

5. A fungicide comprising an effective amount of the compound of formula (I) in claim 1 or a salt thereof.

6. A protozoicide comprising an effective amount of the compound of formula (I) of claim 1 or a salt thereof.

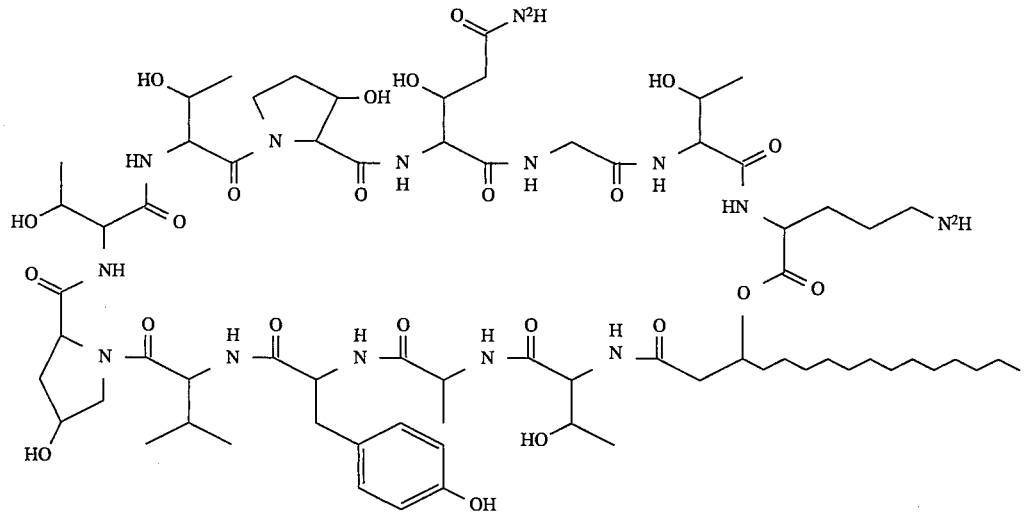

4. The purified cell culture of claim 3, wherein the microorganism is FERM BP-3373.

7. The protozoicide of claim 6, wherein the protozoan is *Pneumocystis carinii*.

* * * * *